United States Patent [19]
Lai et al.

[11] Patent Number: 4,477,665
[45] Date of Patent: Oct. 16, 1984

[54] SUBSTITUTED 2-KETO-1,4-DIAZACYCLOALKANES

[75] Inventors: John T. Lai, Broadview Heights; Pyong-Nae Son, Akron, both of Ohio

[73] Assignee: The B. F. Goodrich Company, Akron, Ohio

[21] Appl. No.: 259,861

[22] Filed: May 4, 1981

[51] Int. Cl.³ .................. C07D 241/04; C07D 401/12
[52] U.S. Cl. ..................................... 544/384; 106/176
[58] Field of Search ........................................... 544/384

[56] References Cited

U.S. PATENT DOCUMENTS

| 3,330,859 | 7/1967 | Dexter et al. | 260/473 |
| 3,531,483 | 9/1970 | Gilles | 260/248 NS |
| 3,567,724 | 3/1971 | Beears | 260/248 NS |
| 3,627,725 | 12/1971 | Gilles | 260/45.85 |
| 3,678,947 | 7/1972 | Kletecka et al. | 260/248 NS |
| 3,694,440 | 9/1972 | Knell et al. | 260/248 NS |
| 3,706,740 | 12/1972 | Dexter et al. | 260/248 CS |
| 3,919,234 | 11/1975 | Ramey et al. | 260/268 TR |
| 3,920,659 | 11/1975 | Ramey et al. | 260/268 TR |
| 3,928,330 | 12/1975 | Ramey et al. | 260/242 |
| 3,928,357 | 12/1975 | Ramey et al. | 544/385 |
| 4,069,195 | 1/1978 | Layer et al. | 260/45.8 NW |
| 4,073,770 | 2/1978 | Son et al. | 260/45.8 NW |
| 4,167,512 | 9/1979 | Lai | 260/239.3 R |
| 4,190,571 | 2/1980 | Lai | 544/385 |
| 4,207,228 | 6/1980 | Lai | 260/45.8 N |

Primary Examiner—Donald G. Daus
Assistant Examiner—S. A. Gibson
Attorney, Agent, or Firm—Nestor W. Shust; Carl W. Battle

[57] ABSTRACT

Disclosed are stabilizer compounds of the formula:

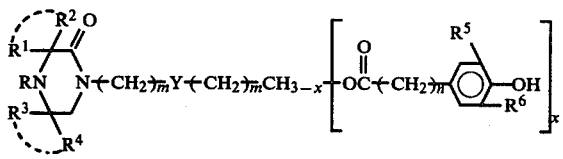

wherein
$R^1$, $R^3$ and $R^6$ are independently selected from the group consisting of alkyl of 1–8 carbon atoms, aryl, cycloalkyl, and alkalene of 2–6 carbon atoms;
$R^2$ is alkyl of 1–6 carbon atoms and can, in conjunction with an acyclic substituent of $R^1$, form a cyclic substituent;
$R^4$ is hydrogen of 1–6 carbon atoms and can, in conjunction with an acyclic substituent of $R^3$, form a cyclic substituent;
$R^5$ is hydrogen or alkyl of 1–6 carbon atoms;
R is hydrogen or alkyl of 1–6 carbon atoms;
Y is oxygen, nitrogen or sulfur;
m is 0 to 6;
n is 0 to 3; and
X is 1 to 3.

The foregoing stabilizers are highly effective in the stabilization of polymeric materials against ultraviolet light and the oxygen present in the environment. Due to the relative bulk of these stabilizers, their resistance to migration within an extraction from the stabilized polymer is similar to the more difficult to prepare polymeric stabilizer.

2 Claims, No Drawings

SUBSTITUTED 2-KETO-1,4-DIAZACYCLOALKANES

BACKGROUND OF THE INVENTION

1. Field of the Invention

This invention relates to the novel dual functional stabilizer compounds, polymeric compositions and methods for the enhancement in the useful life of plastic materials. More specifically, the subject invention is directed to a novel group of esters which possess multiple functional groups including at least one hindered phenol and at least one hindered amine. These esters are highly effective in the stabilization of plastic composition against the degradative forces of ultraviolet light and the oxygen present in the environment.

2. Description of the Prior Art

The increasing use of polymers in the place of the more traditional types of structural materials, (e.g. wood, metals, etc.) has necessitated the compounding of such polymers with a variety of stabilizers in order to enhance their ability to withstand prolonged exposure to a variety of degradative forces. Degradation of such environmentally sensitive polymers can be caused by exposure to light, heat and/or air. Such degradation is usually manifest by either a partial or total loss of structural integrity, changes in light transmission properties, changes in color, loss or reduction in flexibility and/or resiliency, or any combination of the above phenomenon. As will be appreciated, the stabilizers which are used in conjunction with the above polymeric materials, in addition to providing protection against such degradative forces, must also be compatible with the aesthetic properties of the polymeric article formed from such materials and be effective at low concentrations. The economics of the marketplace dictate that these stabilizers be relatively inexpensive and capable of preparation from readily available starting materials by simple and straightforward synthesis techniques.

The prior art is replete with both patents and technical articles describing various stabilizers suitable for use in structural/engineering plastics and in various synthetic fibers. The hindered amine stabilizers are prominently mentioned as suitable in the stabilization of such materials against ultraviolet light degradation. Illustrative of these hindered amines are the decahydroquinolines disclosed in U.S. Pat. Nos. 3,919,234; 3,920,659; 3,928,330; 4,069,195; and 4,073,770; the 1,5-diazacycloalkan-2-ones disclosed in U.S. Pat. No. 4,207,228; and, the 1,4-diazacycloalkan-2-ones disclosed in U.S. Pat. Nos. 4,167,512 and 4,240,961. These hindered amine stabilizers can be prepared in various ways and from various materials.

The prior art also contains a number of disclosures relating to the thermal stabilization of plastics with various phenolic compounds. A number of these phenolic compounds can be described as sterically hindered, (i.e., have substituents pendant from the phenyl nucleus adjacent to hydroxy substituent). Typically such hindered phenolic antioxidants are only suitable for the inhibition of oxidation of plastics and are used in conjunction with other stabilizers (i.e., UV stabilizers). Representative of the patent literature relating to phenolic antioxidants are U.S. Pat. Nos. 3,330,859 and 3,627,725 (phenolic functional esters); U.S. Pat. Nos. 3,706,740, 3,567,724 and 3,694,440 (phenolic functional triazines); and U.S. Pat. Nos. 3,531,483 and 3,678,047 (phenolic functional isocyanurates).

It is not unusual for a number of the ultraviolet light stabilizers and antioxidants referred to hereinabove to be bimodal in their activity; that is, possess a primary activity for inhibition of degradation from one type of degradative force or agent and a lesser degree of activity for inhibition of degradation from a different type of source or agent. Typical of such compounds are those disclosed in U.S. Pat. No. 3,678,047; which include within its scope the commercial product Goodrite® 3125 (available from The BFGoodrich Company, Akron, Ohio). Goodrite® 3125 is sold primarily as an antioxidant although it does also exhibit a lesser degree of effectiveness in the inhibition of ultraviolet degradation. In practice, Goodrite® 3125 is used in combination with a UV stabilizer such as CYASORB® 531 (available from The American Cyanamide Company, Wayne, N.J.).

As is readily appreciated by the prior art relating to polymer stabilization, a compound's activity cannot be readily predicted from its structure. Such unpredictability pertains not only to compounds where a single, or principal activity is anticipated, but to compounds which one would anticipate to possess bimodal activity. For example, the compounds disclosed in U.S. Pat. No. 3,919,234 are prepared by alkylation of a piperazine dione with a 2,6-dialkylsubstituted hydroxyphenylalkylhalide. The resultant compound thus obtained has a functional substituent containing a hindered phenol. Yet, such compounds reportedly are only principally effective as UV stabilizers and must be used in conjunction with antioxidants if thermal oxidation of a stabilized resin is to be prevented.

The use of more than one stabilizer in a resin compound is not at all an uncommon practice, however, such practice does increase the cost of the resin and may introduce processing problems and alteration of the resins' physical properties and aesthetic characteristics.

It would, thus, be highly desirable to be able to stabilize a polymeric resin against degradation using the minimum number of ingredients at the lowest possible concentration.

SUMMARY OF THE INVENTION

Accordingly, it is the object of this invention to remedy the above as well as related deficiencies in the prior art.

More specifically, it is the principal object of this invention to provide stabilizer compounds which are effective for inhibition of degradation of organic polymeric materials by ultraviolet light and the oxygen present in the environment (hereinafter referred to as "bimodal stabilizer").

Another object of this invention is to provide organic polymeric compositions which are stabilized against degradation by ultraviolet light and the oxygen present in the environment.

Yet another object of this invention is to provide a method for the stabilization of organic polymeric materials from degradation by ultraviolet light and the oxygen present in the environment.

The foregoing and related objects are achieved by providing stabilizer compounds of the formula:

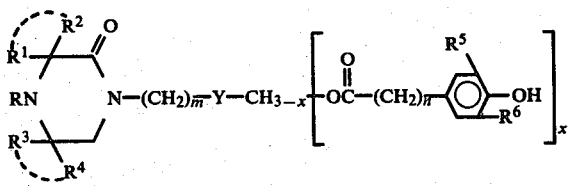

wherein
R$^1$, R$^3$ and R$^6$ are independently selected from the group consisting of alkyl of 1–8 carbon atoms, aryl, cycloalkyl, and alkalene of 2–6 carbon atoms;
R$^2$ is alkyl of 1–6 carbon atoms and can, in conjunction with an acyclic substituent of R$^1$ form a cyclic substituent;
R$^4$ is alkyl of 1–6 carbon atoms and can, in conjunction with an acyclic substituent of R$^3$, form a cyclic substituent;
R$^5$ is hydrogen or alkyl of 1–6 carbon atoms;
R is hydrogen or alkyl of 1–6 carbon atoms;
Y is oxygen, nitrogen or sulfur;
m is 0 to 6;
n is 0 to 3; and
X is 1 to 3;

The foregoing stabilizers are highly effective in the stabilization of polymeric materials against ultraviolet light and the oxygen present in the environment. Due to the relative bulk of these stabilizers, their resistance to migration within and extraction from the stabilized polymer is similar to the more difficult to prepare polymeric stabilizer.

DESCRIPTION OF THE INVENTION INCLUDING PREFERRED EMBODIMENTS

The bimodal stabilizers of this invention can be readily prepared by direct esterification of a carboxylic acid functional phenol and a hindered amine functional alkanol, in the presence of catalyst and mineral acid, under the appropriate conditions.

The carboxylic acid functional phenols which can be used in the synthesis of the stabilizers of this invention can be prepared by the following structural formula

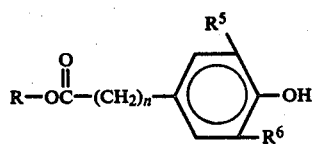

wherein
R is hydrogen or alkyl of 1–6 carbon atoms;
R$^5$ is hydrogen or alkyl of 1–6 carbon atoms;
R$^6$ is independently selected from the group consisting of alkyl of 1–8 carbon atoms, aryl, cycloalkyl, and alkalene of 2–6 carbon atoms;
n is 0 to 3

The foregoing carboxylic acid functional phenols can be readily prepared from readily available materials utilizing standard equipment and traditional synthesis procedures. In addition, a number of the compounds within the foregoing formula are available commercially.

Representative of the carboxylic acid functional phenols which are suitable for use in the preparation of the stabilizer of this invention include: β(3,5-di-t-butyl-4-hydroxy-phenyl) propionic acid; β-(3,5-di-t-pentyl-4-hydroxy-phenyl) propionic acid; and 3,5-di-t-butyl-4-hydroxy-benzoic acid.

The hindered amine functional alkanols which can be used in the synthesis of the stabilizer of this invention can be represented by the following formula

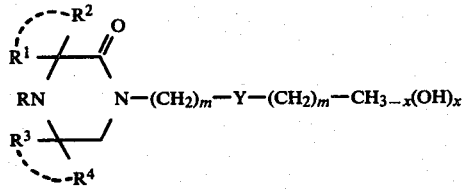

wherein
R$^1$ and R$^3$ are independently selected from the group consisting of alkyl of 1–8 carbon atoms, aryl, cycloalkyl, and alkalene of 2–6 carbon atoms;
R$^2$ is alkyl of 1–6 carbon atoms and can, in conjunction with an acyclic substituent of R$^1$, form a cyclic substituent;
R$^4$ is alkyl of 1–6 carbon atoms and can, in conjunction with an acyclic substituent of R$^3$, form a cyclic substituent; and
R is hydrogen or alkyl of 1–6 carbon atoms
Y is oxygen, nitrogen and sulfur; and
m is 0 to 6.
X is 1 to 3.

The foregoing hindered amine functional alkanols can be prepared from readily available starting materials utilizing standard equipment and synthesis disclosed in the open literature. For example, Example V-B of U.S. Pat. No. 4,167,512 discloses the synthesis of β(3,3,5,5-tetramethyl-piperazin-2-one) iso-butanol. Utilizing analogous procedures, many of the alkanols within the foregoing formula can be prepared according to the teachings of the above patent, which is hereby incorporated by reference in its entirety.

Representative of the hindered amine functional alkanols which are suitable for use in preparation of the stabilizers of this invention include: β(3,3,5,5-tetramethyl-piperazin-2-one)iso-butanol; 2-[2-(3,3,5,5-tetramethyl-2-oxy-piperazinyl)-ethoxy]-ethanol; and β-(3,3-dimethyl-5,5-pentamethylene-piperazin-2-one)-isobutanol.

As noted hereinabove, the direct esterification of the carboxylic acid functional phenol by the hindered amine functional alkanol occurs in the presence of a strong mineral acid, typically sulfuric acid, and an appropriate catalyst.

The catalyst suitable for use in the synthesis of the stabilizer of this invention is typically a material effective for the condensation of an alcohol and acid to yield the desired ester. Transesterification catalysts, including Lewis Acids, are highly effective in directing the reaction of the acid functional phenol and amine functional alkanol in favor of the desired bimodal stabilizer products. Representative of catalysts which are suitable for use in the synthesis of the stabilizers of this invention include: titanium isopropoxide; stannic chloride; or aluminum chloride.

Typically, the foregoing reactants, catalysts and compatible reaction medium are charged to a reactor, such as a round-bottomed flask, equiped with a reflux condenser, a magnetic stirrer and gas inlet, the reactor purged of air with an inert gas (i.e. Argon). The contents of the flask are, thereafter, heated under reflux conditions with stirring and under an Argon blanket. The conditions prevailing during such synthesis can be readily controlled and the reaction generally proceeds at atmospheric pressure. The reaction temperature is not critical, however, in order to assure both satisfactory yield and efficiency of synthesis, such synthesis is carried out at the refluxing temperature of the reaction medium which can range from about 80° to about 150° C.

Often times one or more of the reactants themselves (i.e., the alkanol amine) can serve as the medium for the conduct of the synthesis of this invention. Alternatively, such synthesis can also be satisfactorily conducted in an organic solvent; provided, such solvent is inert toward both the reactants and product of the synthesis under the anticipated reaction conditions. Typical organic solvents which can be used in this process include the common aromatic and paraffinic solvents such as benzene, p-xylene, toluene, dichloromethane, chlorobenzene, cyclohexane and the like.

Once the desired compound has been prepared from the aforementioned materials in accordance with the above process, it can be readily recovered from the reaction medium by conventional means.

The compounds prepared as described above are highly effective in the stabilization of photodegradable organic polymeric material from the deteriorating effects of ultraviolet light.

The term "photodegradation" as used herein is intended as descriptive of any photoinduced changes in the physical, chemical and/or electrical properties of such organic polymeric materials upon their exposure to sufficient quanities of ultraviolet light. Such degradation can typically include crosslinking of the polymer, dehydrohalogenation, reduction in chain length, photooxidation and the like. Polymers which are especially sensitive to ultraviolet light degradation are materials which contain unsaturation along their respective backbones, such as cispolyisoprene, styrene/butadiene copolymer, vinyl halide polymers, polyolefins, polyacetaldehydes, polyurethanes, ABS resins, polystyrene, polyacrylonitrile, polycarbonates, polyacrylates, poly-α-alkyl-acrylates, varnish, phenolformaldehyde resins, polyepoxides, polyesters, and their respective blends and copolymers. The compounds prepared according to the process of this invention are especially effective in the stabilization of the poly-α-monoolefins such as polymers derived from ethylene, propylene, isobutylene, 1-butene, 1-pentene, 1-hexane, 4-methyl-1-pentene and the like.

In addition to the stabilizers prepared according to the process of this invention, a typical organic polymeric material can contain common compounding ingredients and additional stabilizers for the protection of such polymer against various other degradative forces and agents.

Representative compounding ingredients can include metal oxides, such as zinc, calcium and magnesium oxide, fatty acids such as stearic, lauric acid and the metal salts thereof; fillers such as calcium and magnesium carbonate, calcium and barium sulfonates, aluminum silicates, asbestos, and the like; plasticizers and extenders, such as dialkyl and diaryl organic acids, such as diisobutyl, diisooctyl, diisodecyl and dibenzyl oleates, stearates, sebacates, azelates, phthalates, and the like; ASTM Type 2 petroleum oils, paraffinic oils, castor oil, tall oil, glycerine, and the like; antioxidants, such as 2,6-di-t-butyl phenol, 2,2'-thio-bis-(4-methyl-6-t-butyl phenol), 2,2'-methylene-bis-6-t-butyl-4-ethyl phenol, 4,4'-butyldiene-bis-6-t-butyl-m-cresol, 2-(4-hydroxy-3,5-di-t-butylanilino-4,6-bis(octylthio)1,3,5-triazine, hexahydro-1,3,5-tris-β-(3,5-di-t-butyl-4-hydroxybenzyl)-isocyanurate, tetrakismethylene-3(3', 5'-di-t-butyl-4'-hydroxyphenyl) propionate methane, distearylthiodipropionate, dilaurylthiodipropionate, tri(nonylphenyl) phosphite, tin thioglycolate, and the like; and other ingredients such as pigments, tackifiers, flame retardants, fungicides, and the like.

The stabilizers of this invention, together with other optional additive and compounding agents of the type described hereinabove, can be combined with ultraviolet light and thermally sensitive polymeric resins in accordance with standard mixing techniques and equipment; such as in a Banbury mixer, a Henschel mixer, a rubber mill, an extruder mixer or equivalent device. The various components of the composition may be physically intimately blended either in the absence of or in the presence of a common solvent; or in a solvent which is capable of dissolving the polymer component of the composition yet substantially incapable of dissolving the stabilizer ingredients. Typical of such solvent/dispersing agents include hexane or benzene. Subsequent to intimately dispersing the various components of the composition within one another, the dispersing agent (if any) can be removed by selective evaporation and the resultant resin recovered. The resin may thereafter be formed into useable products by a variety of standard techniques.

The ultraviolet light stability of the compositions of this invention is evaluated by exposing samples of a photosensitive plastic, with and without stabilizer, to a Xenon or carbon arc light in a Weather-Ometer operating at temperatures of about 60° C. The sample is considered to have been photodegraded when it has lost in excess of fifty percent (50%) of its tensile strength as determined by ASTM D 638-76. In a typical test protocol, a pre-selected quantity of bimodal stabilizer and other optional processing aids (if any) are compounded with an unstabilized photosensitive resin, such as polypropylene, and the compounded resin compression molded into sheets approximately 20 mils in thickness. Several sheets of plastic are usually prepared in the above manner, each having different stabilizers, at different concentrations. Subsequent to formation of the foregoing compounded resin into sheet material, a series of dumb bells are cut from each sheet and placed in a Wheather-Ohmeter. At 500 hours, or other pre-selected intervals, one (1) dumb bell of each sample of compounded resin is removed from the Weather-Ohmeter and its tensile strength measured on an Instron tensile testing device. The tensile strength of each sample is then compared to the values obtained from a sample cut from the same sheet which had not experienced any UV exposure. The sample is considered to have been photodegraded when it has experienced in excess of fifty percent (50%) reduction in its tensile strength.

The resistance of samples of compounded resin to thermal degradation can be readily determined by standard oven aging techniques. Sample failure is calculated as the average length of time between the initial onset of physical deterioration (usually manifest as discoloration in crazing) and the sample failure (usually manifest by fracturing or cracking).

EXAMPLES

The Examples which follow further define, describe and illustrate the (i) preparation of the novel compounds of this invention and (ii) evaluation of such compounds as stabilizers of polymeric resins against both ultraviolet light and oxidative degradation. Apparatus and procedures used in both the preparation and evaluation of these novel stabilizers are standard or as hereinbefore described. Parts and percentages appearing in such Examples are by weight unless otherwise indicated.

EXAMPLE I

Preparation of
2,2-dimethyl-2-3,3,5,5-tetramethyl-2-oxo-1-piperazinyl) ethyl B-(3,5-di-t- butyl-4-hydroxyphenyl propionate)

Into a single necked round bottom flask, equipped with a magnetic stirrer, reflux condensor, an Argon inlet and a Dean-Stark trap are charged 4.57 grams $\beta$(3,3,5,5-tetramethyl-piperazin-2-one) iso-butanol, 5.57 grams $\beta$(3,5-di-t-butyl-4-hydroxy-phenyl) propionic acid, 40 milliliters xylene and 0.57 grams titanium tetraisopropoxide. The flask is thereupon purged of air with Argon, heated under refluxing conditions and reaction allowed to proceed, at reflux, overnight. Water is removed from the reaction medium via the Dean-Stark trap. The following morning, the reaction mass was treated with 20 milliliters of toluene and 40 milliliters of water and then the solids separated therefrom by filtration. The filtrate is collected, washed with 20 milliliters of saturated aqueous sodium chloride solution and the aqueous and organic phase separated from one another. The organic phase is dried over sodium sulfate overnight and thereafter filtered. The filtrate is conentrated by roto-evaporation and placed under a vacuum for removal of volatile residues leaving a dark orange oily substance. Hexane is added to the oily substance, resulting in precipitation of a white solid. This solid is recovered by filtration, recrystalized from hexane and toluene and washed (×2) with hexane for removal of trace of orange colored residues. The IR spectra and elemental analysis of the product thus obtained are consistent with the structure of the title compound, Mp 75°–78° C.

EXAMPLE II

Preparation of
2,2-dimethyl-2-(3,3,5,6,6-pentamethyl-2-oxo-piperazinyl) ethyl B-(3,5-di-t-butyl-4-hydroxyphenyl propionate)

The procedures of Example I are repeated except for the substitution of $\beta$(3,3,5,5-tetramethyl-N-methyl-piperazin-2-one) iso-butanol for $\beta$(3,3,5,5-tetramethyl-piperazin-2-one) iso-butanol. The IR spectra and elemental analysis of the product thus obtained are consistent with the structure of the title products, Mp 90°–92° C.

The compounds of Examples I and II are incorporated within an environmentally sensitive plastic resin (polypropylene) in the manner previously set forth and the resultant mixture compression molded into films approximately twenty (20) mils in thickness. Several dumb bells are cut from these films. This procedure is repeated with the additional plastic resin with and without commercially available stabilizers and the resinous material thereafter formed into films of equivalent thickness. A series of dumb bells are also cut from these latter films. The films containing the bimodal stabilizer of this invention, films devoid of stabilizer and films containing commercially available stabilizer are evaluated for their resistance to UV degradation and oxidative degradation in the manner heretofor described. The table which follows illustrates the comparative effectiveness of the stabilizers of this invention in relation to the unstabilized films and the films stabilized with commercially available materials.

| Sample | Stabilizer | Concentration (phr) | Oven Aging+ @ 125° C. | Xenon Exposure+ |
|---|---|---|---|---|
| (a) | Compound of Example I | 0.1 | 5 | 480 |
| (b) | Compound of Example II | 0.1 | 6 | 540 |
| (c) | Compound of Example I | 0.1 | 42 | 820 |
|  | Goodrite 3114 | 0.1 |  |  |
| (d) | Compound of Example II | 0.1 | 43 | 900 |
|  | Goodrite 3114 | 0.1 |  |  |
| (e) | Goodrite 3114 | 0.1 | 32 | 380 |
| (f) | None | — | 1 | 200 |

+number of hours before sample deemed to have failed.

The foregoing comparison clearly indicates that the bimodal stabilizers of this invention are highly effective and demonstrate a degree of synergy when used in conjunction with the commercially available antioxidant Goodrite 3114.

The foregoing examples have been provided as illustrative of some of the preferred embodiments of this invention and are not intended as delineating its scope which is set forth in the following claims.

We claim:

1. The compound which is 2,2-dimethyl-2-(3,3,5,5-tetramethyl-2-oxo-1-piperazinyl)ethyl $\beta$-(3,5-di-t-butyl-4-hydroxyphenyl propionate).

2. The compound which is 2,2-dimethyl-2-(3,3,4,5,5-pentamethyl 2-oxo-1-piperazinyl)ethyl $\beta$-(3,5-di-t-butyl-4-hydroxyphenyl propionate).

* * * * *

UNITED STATES PATENT AND TRADEMARK OFFICE
CERTIFICATE OF CORRECTION

PATENT NO. : 4,477,665
DATED : October 16, 1984
INVENTOR(S) : JOHN TA-YUAN LAI and PYONG-NAE SON It is certified that error appears in the above-identified patent and that said Letters Patent are hereby corrected as shown below:

In Claim 2, line 2 "pentamethyl  2-oxo-1-piperazinyl)ethyl"

should read --pentamethyl-2-oxo-1-piperazinyl)ethyl--

Signed and Sealed this

Twenty-first Day of January 1986

[SEAL]

Attest:

DONALD J. QUIGG

Attesting Officer

Commissioner of Patents and Trademarks